US 6,713,047 B1

(12) United States Patent
Lewis et al.

(10) Patent No.: US 6,713,047 B1
(45) Date of Patent: Mar. 30, 2004

(54) PHARMACEUTICAL AEROSOL COMPOSITION CONTAINING HFA 227 AND HFA 134A

(75) Inventors: David Lewis, Parma (IT); David Ganderton, Devon (GB); Brian Meakin, Claverton Down Bath (GB); Paolo Ventura, Parma (IT); Gaetano Brambilla, Parma (IT); Raffaella Garzia, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 09/831,886

(22) PCT Filed: Nov. 22, 1999

(86) PCT No.: PCT/EP99/08959

§ 371 (c)(1),
(2), (4) Date: Nov. 30, 2001

(87) PCT Pub. No.: WO00/30607

PCT Pub. Date: Jun. 2, 2000

(30) Foreign Application Priority Data

Nov. 25, 1998 (IT) .......................................... MI98A2558

(51) Int. Cl.$^7$ .............................. A61K 9/12; A61K 9/72
(52) U.S. Cl. ............................ 424/45; 424/43; 424/46; 424/450; 424/489; 128/203.15
(58) Field of Search ............................ 424/45, 489, 43, 424/450, 46; 128/203.15

(56) References Cited

U.S. PATENT DOCUMENTS 6,004,537 A    12/1999   Blondino et al.

FOREIGN PATENT DOCUMENTS

| EP | 0 653 204 | 5/1995 |
| GB | 2 326 334 | 12/1998 |
| GB | WO 0147493 A1 * | 7/2001 |
| WO | WO 96/32099 | 10/1996 |
| WO | WO 97/47286 | 12/1997 |
| WO | WO 98/01147 | 1/1998 |
| WO | WO 98/13031 | 4/1998 |

* cited by examiner

Primary Examiner—Michael G. Hartley
Assistant Examiner—M. Haghighation
(74) Attorney, Agent, or Firm—Oblon, Spivak, McClelland, Maier & Neustadt, P.C.

(57) ABSTRACT

In a solution composition for use in an aerosol inhaler which comprises an active material, a propellant containing a hydrofluoroalkane, a cosolvent and optionally a low volatility compound the use of a mixture of HFA 134a and HFA 227 allows to modulate the mass median aerodynamic diameter (MMAD) of the aerosol particles on actuation of the inhaler to target specific regions of the respiratory tract. Moreover the fine particle dose (FPD) of the active ingredient in the composition increases by reducing the metering chamber volume.

29 Claims, No Drawings

PHARMACEUTICAL AEROSOL COMPOSITION CONTAINING HFA 227 AND HFA 134A

The invention relates to aerosol compositions for pharmaceutical use. In particular, this invention relates to aerosol compositions for use in pressurised metered dose inhalers (MDIs). The invention also relates to solution aerosol compositions, wherein the propellant comprises HFA 134a or HFA 227 or their mixtures.

Another aspect of the invention relates to pressurised MDIs for dispensing said compositions.

Inhalers are well known devices for administering pharmaceutical products to the respiratory tract by inhalation.

Active materials commonly delivered by inhalation include bronchodilators such as β2 agonists and anticholinergics, corticosteroids, anti-leukotrienes, anti-allergics and other materials that may be efficiently administered by inhalation, thus increasing the therapeutic index and reducing side effects of the active material.

There are a number of types of inhaler currently available. The most widely used type is a pressurised metered dose inhaler (MDI) which uses a propellant to expel droplets containing the pharmaceutical product to the respiratory tract as an aerosol. Formulations used in MDIs (aerosol formulations) generally comprise the active material, one or more liquefied propellants and a surfactant or a solvent.

For many years the preferred propellants used in aerosols for pharmaceutical use have been a group of chlorofluorocarbons which are commonly called Freons or CFCs, such as $CCl_3F$ (Freon 11 or CFC-11), $CCl_2F_2$ (Freon 12 or CFC-12), and $CClF_2$-$CClF_2$ (Freon 114 or CFC-114). Chlorofluorocarbons have properties particularly suitable for use in aerosols, including high vapour pressure which generates clouds of droplets of a suitable particle size from the inhaler.

Recently, the chlorofluorocarbon (CFC) propellants such as Freon 11 and Freon 12 have been implicated in the destruction of the ozone layer and their production is being phased out.

Hydrofluoroalkanes [(HFAs) known also as hydrofluorocarbons (HFCs)] contain no chlorine and are considered less destructive to ozone and these are proposed as substitutes for CFCs.

HFAs and in particular 1,1,1,2-tetrafluoroethane (HFA 134a) and 1,1,1,2,3,3,3-heptafluoropropane (HFA 227) have been acknowledged to be the best candidates for non-CFC propellants and a number of medicinal aerosol formulations using such HFA propellant systems are disclosed in several patent applications.

Many of these applications, in which HFAs are used as propellant, propose the addition of one or more of adjuvants including compounds acting as cosolvents, surface active agents including fluorinated and non-fluorinated surfactants, dispersing agents including alkylpolyethoxylates and stabilizers.

Cosolvents which may be used in these formulations include alcohols such as ethanol and polyols such as propylene glycol.

Medicinal aerosol formulations using such propellant systems are disclosed in, for example, EP 0372777. EP 0372777 requires the use of HFA 134a as a propellant in combination with both a surfactant and an adjuvant having higher polarity than the propellant.

For aerosol suspension compositions, a surfactant is often added to improve the physical stability of the suspension. EP 0372777 states that the presence of surfactant assists in the preparation of stable, homogeneous suspensions and may also assist in the preparation of stable solution formulations.

Surfactants also lubricate the valve components in the inhaler device.

The use of propylene glycol as a solvent having a higher polarity than the propellant in HFA pressurised metered dose inhalers formulations has been mentioned in several other patent applications and for example in:

EP 504112 relates to a pharmaceutical aerosol formulation free from CFCs containing a propellant (hydrocarbon, HFA or a mixture), one or more pharmaceutical active ingredients, a non-ionic surfactant and optionally other conventional pharmaceutical auxiliaries suitable for aerosol formulations comprising solvents having a higher polarity than the propellant, other non-ionic surfactants as valve lubricants, vegetable oils, phospholipids, taste masking agents.

DE 4123663 describes a medical aerosol composition containing a dispersion or suspension of an active agent in association with a compound with surface-active or lipophilic properties, heptafluoropropane as propellant and an alcohol such as ethanol and/or propylene glycol.

Other applications propose the addition of dispersing agents to the composition. U.S. Pat. No. 5,502,076 concerns compositions used in inhalation aerosols comprising an HFA, leukotriene antagonists and dispersing agent comprising 3C-linked triesters, vitamin E acetate, glycerin, t-BuOH, or transesterified oil/polyethylene glycol.

EP 384371, describes a propellant for an aerosol, comprising pressure-liquefied HFA 227 in a mixture with pressure-liquefied propane and/or n-butane and/or iso-butane and/or dimethyl ether and/or 1,1-difluoroethane. The document also discloses foam formulations (shaving and shower foams) containing glycerol as additive.

The effectiveness of an aerosol device, for example an MDI, is a function of the dose deposited at the appropriate site in the lungs. Deposition is affected by several parameters, of which the most important are the Fine Particle Dose (FPD) and the aerodynamic particle size. Solid particles and/or droplets in an aerosol formulation can be characterized by their mass median aerodynamic diameter (MMAD, the diameter around which the mass aerodynamic diameters are distributed equally)

The FPD gives a direct measure of the mass of particles within a specified size range and is closely related to the efficacy of the product.

Particle deposition in the lung depends largely upon three physical mechanisms: (1) impaction, a function of particle inertia; (2) sedimentation due to gravity; and (3) diffusion resulting from Brownian motion of fine, submicrometer (<1 $\mu$m) particles. The mass of the particles determines which of the three main mechanisms predominates.

The effective aerodynamic diameter is a function of the size, shape and density of the particles and will affect the magnitude of forces acting on them. For example, while inertial and gravitational effects increase with increasing particle size and particle density, the displacements produced by diffusion decrease. In practice, diffusion plays little part in deposition from pharmaceutical aerosols. Impaction and sedimentation can be assessed from a measurement of the mass median aerodynamic diameter (MMAD) which determines the displacement across streamlines under the influence of inertia and gravity, respectively.

Aerosol particles of equivalent MMAD and GSD (Geometric Standard Deviation) have similar deposition in the lung irrespective of their composition. The GSD is a measure of the variability of the aerodynamic particle diameters.

For inhalation therapy there is a preference for aerosols in which the particles for inhalation have a diameter of about 0.8 to 5 µm. Particles which are larger than 5 µm in diameter are primarily deposited by inertial impaction in the oropharynx, particles 0.5 to 5 µm in diameter, influenced mainly by gravity, are ideal for deposition in the conducting airways, and particles 0.5 to 3 µm in diameter are desirable for aerosol delivery to the lung periphery. Particles smaller than 0.5 µm may be exhaled.

Respirable particles are generally considered to be those with aerodynamic diameters less than 5 µm. These particles, particularly those with a diameter of about 3 µm, are efficiently deposited in the lower respiratory tract by sedimentation.

Besides the therapeutic purposes, the size of aerosol particles is important in respect to the side effects of the drugs. For example, it is well known that the oropharynx deposition of aerosol formulations of steroids can result in side effects such as candidiasis of mouth and throat.

On the other hand a higher systemic exposure to the aerosol particles due to deep lung penetration can enhance the undesired systemic effects of the drugs. For example, the systemic exposure to steroids can produce side effects on bone metabolism and growth.

It has been reported that the particle size characteristics of HFA aerosol formulations of the state of the art are often very different from the products to be replaced.

HFA substitutes may not be pharmaceutically or clinically equivalent and adjustment of dose and regimen may be necessary, giving problems for doctor, pharmacist and patient.

An alternative is the seamless transition from the old to the new formulas which demands the same deposition of the drug in the lung. For any product, this can be inferred from the amount of drug and its particle size distribution in the aerosol cloud. Matching CFC and HFA formulations with suspension technology is practicable because the particle size of the aerosol cloud is dominated by the particle size of the suspended drug, defined by the milling or precipitation process.

However, when, as commonly occurs, solution formulations are unavoidable, the volumetric contribution of suspended particles is absent and much finer clouds, largely defined by the concentration of the drug in the solution, are generated. In these circumstances, a cosolvent, such as alcohol, is often added to ensure satisfactory solubility. The fine clouds from such formulations give more extensive deposition in the lung periphery than their CFC counterparts.

EP 0553298 describes an aerosol formulation comprising: a therapeutically effective amount of beclomethasone 17,21 dipropionate (BDP); a propellant comprising a hydrofluorocarbon selected from the group consisting of HFA 134a, HFA 227, and a mixture thereof, and ethanol in an amount effective to solubilize the beclomethasone 17,21 dipropionate in the propellant. The formulation is further characterized in that substantially all of the beclomethasone 17,21 dipropionate is dissolved in the formulation and that the formulation contains no more than 0,0005% by weight of any surfactant.

It has been reported in literature that these new formulations of beclomethasone dipropionate (BDP) as a solution in HFA 134a deliver a particle size distribution with a MMAD of 1.1 µm. This means that the peripheral pulmonary deposition of very small particles increases and submicronic particles can easily be directly absorbed from the alveoli into the bloodstream. The rate and extent of systemic absorption is significantly increased and as a consequence undesired effects for example certain side effects can increase. A relatively large fraction of the dose is exhaled. The implications of this for clinical efficacy and toxic effects are great. They arise because the principles of formulation using HFAs may modify the physical form of the respired cloud.

It has now been surprisingly found that in solution formulations of the present application comprising an active material, a propellant containing a hydrofluoroalkane (HFA), a cosolvent and optionally a low volatility compound, the use of a mixture of HFA 134a and of HFA 227 allows the modulation of the MMAD of the aerosol particles on actuation of the inhaler to a value which is suited for the pulmonary administration.

Mixtures of hydrofluoroalkanes have been previously used in suspension-based pMDI compositions to vary the density of the continuous phase in order to match the density of the suspended drug and maximize the physical stability of the pMDI suspension.

Williams R. O. et al. in Drug Dev. Ind. Pharm. 24 (8), 763–770, 1998 investigated the influence of propellant composition on the characteristics of suspension aerosol compositions. The results showed that as the density of the propellant blends approached the density of the suspended drug particles, the formulation became more physically stable.

Analogously, WO93/11747 discloses that in suspension aerosol compositions the density of the propellant may be changed by using HFA 134a and HFA 227 mixtures so as to bring it to approximately the same value of the density of the active ingredient, minimizing thereby the sedimentation of the drug particles.

Therefore the aerosol compositions using the new propellant systems disclosed in the known prior art seek to overcome problems of physical stability of the formulations.

It has surprisingly been found that in solution compositions by using a mixture of HFA 134a and HFA 227 and optionally a low volatility component, the MMAD of the aerosol particles on actuation of the inhaler can be modulated and thus the compositions may be formulated so that the aerodynamic particle size characteristics are optimized.

Advantageously, the low volatility component has a vapour pressure at 25° C. not more than 0.1 kPa, preferably not more than 0.05 kPa.

The low vapour pressure of the low volatility component is to be contrasted with that of the cosolvent which preferably has a vapour pressure at 25° C. not less than 3 kPa, more preferably not less than 5 kPa.

The cosolvent has advantageously a higher polarity than that of the propellant and the cosolvent is used to increase the solubility of the active material in the propellant.

Advantageously the cosolvent is an alcohol. The cosolvent is preferably ethanol. The cosolvent may include one or more materials.

The low volatility component may be a single material or a mixture of two or more materials.

In general terms the low volatility component can be any compound, safe and compatible with the propellant system of the invention capable to influence either the size or the density of the aerosol particle so affecting the MMAD.

We have found that glycols are particularly suitable for use as the low volatility component, especially propylene glycol, polyethylene glycol and glycerol.

Other particularly suitable materials are thought to include other alcohols and glycols, for example alkanols such as decanol (decyl alcohol), sugar alcohols including sorbitol, mannitol, lactitol and maltitol, glycofural (tetrahydro-furfurylalcohol) and dipropylene glycol.

The low volatility component may include esters for example ascorbyl palmitate and tocopherol. Among the esters isopropyl myristate is particularly preferred.

It is also envisaged that various other materials may be suitable for use as the low volatility component including vegetable oils, organic acids for example saturated carboxylic acids including lauric acid, myristic acid and stearic acid; unsaturated carboxylic acids including sorbic acid, and especially oleic acid, which has been previously used in aerosol formulations, in order to improve the physical stability of drug suspensions, as a dispersing agent useful in keeping the suspended particles from agglomerating; saccharine, ascorbic acid, cyclamic acid, amino acids or aspartame; alkanes for example dodecane and octadecane; terpenes for example menthol, eucalyptol, limonene; sugars for example lactose, glucose, sucrose; polysaccharides for example ethyl cellulose, dextran; antioxidants for example butylated hydroxytoluene, butylated hydroxyanisole; polymeric materials for example polyvinyl alcohol, polyvinyl acetate, polyvinyl pyrollidone; amines for example ethanolamine, diethanolamine, triethanolamine; steroids for example cholesterol, cholesterol esters.

The amount of low volatility component in the composition depends to some extent upon its density and the amount of active material and cosolvent in the composition. Advantageously, the composition includes not more than 20% by weight of the low volatility component. Preferably the composition includes not more than 10% by weight of the low volatility component.

On actuation of the inhaler, the propellant and the ethanol vaporise but because of the low vapour pressure of the low volatility component, that component generally will not.

It is thought that it is preferable for the composition to contain at least 0.2%, preferably at least 1% by weight of the low volatility component. The composition may contain between 1% and 2% by weight.

According to the present invention, as it can be noticed from the results reported in the tables, the influence on the MMAD of the particles is correlated to the ratio of the two HFA components (as well as to the amount and density of the low volatility component).

The MMAD can be modulated by changing the ratio between HFA 134a and HFA 227; said ratio may range from 10:90 to 90:10.

From the data reported in Table 1, it is clear that MMAD is increased by increasing the proportion of HFA 227 in the mixture.

Most advantageously, the composition is such that, on actuation of the aerosol inhaler in use, the MMAD of the aerosol particles is not less than 2 $\mu$m. For some active materials the MMAD is preferably not less than 2.5 $\mu$m and for a few formulations, the preferred MMAD will be greater than 3 $\mu$m or even greater than 4 $\mu$m.

In some cases a small quantity of water may be added to the composition to improve the solution of the active material and/or the low volatility component in the cosolvent.

The active material may be one or more of any biologically active material which could be administered by inhalation. Active materials commonly administered in that way include $\beta 2$ agonists, for example salbutamol and its salts, steroids for example beclomethasone dipropionate or anticholinergics for example ipratropium bromide and combinations thereof.

As indicated above, on actuation of the inhaler, the aerosol particles advantageously have an MMAD of not less than 2 $\mu$m, for many formulations more preferably not less than 2.5 $\mu$m.

It has also been found, and it is a further object of the invention, that it is possible to increase the "fine particle dose" or FPD of the active ingredients in the compositions of the invention, without affecting MMAD, by decreasing the metering chamber volume of the metered dose inhaler (increasing thereby the space above it named "sump") and/or changing the ratio between the metering chamber and the space above by increasing the sump. In particular, by reducing the metering chamber volume from 50 $\mu$l to 25 $\mu$l at sump volume constant, it is possible to increase the fine particle delivery up to 40%.

This result could be only obtained with solution compositions in which the MMAD of the particles is higher than 2 $\mu$m and it is particularly surprising since it is known from Williams R. O. et al. in Pharmaceutical Research 14 (4), 438–443, 1997 that in suspension based pMDI containing HFA 134a the aerodynamic particle size distribution was not influenced as the metering chamber volume of the valve was increased.

The solution formulations with MMAD>2 may be obtained by using a metering chamber <40 $\mu$l, preferably 25 $\mu$l: the fine particle delivery (Stage 3 to filter; <4.7 $\mu$m) determined through a Andersen Cascade Impactor is increased by at least 10% in comparison with the same formulation packaged with a valve with a metering chamber of at least 50 $\mu$l and the same sump, as it will be shown hereinbelow.

Using a reduced metering chamber volume (e.g. about 40 $\mu$l or lower for a conventional inhaler), favourable results are obtained even with aerosol compositions wherein the propellant consists either in HFA 227 or in HFA 134a alone.

Also provided is a method of filling an aerosol inhaler with a composition, the method comprising filling the following components into the inhaler (a) one or more active materials, (b) optionally one or more low volatility components, (c) one or more cosolvents followed by the addition of a propellant containing a hydrofluoroalkane (HFA) or a mixture of HFAs.

Embodiments of the invention will now be described by way of example.

The aerosol compositions of the invention described below were prepared by the following method. The required components of a composition were added into a can in the following order: drug, non-volatile additive, absolute ethanol. After crimping of the valve on to the can, the propellant was added through the valve. The weight gain of the can after each component was added was recorded to allow the percentage, by weight, of each component in the formulation to be calculated.

The aerodynamic particle size distribution of each formulation was characterized using a Multistage Cascade Impactor according to the procedure described in the European Pharmacopoeia 2nd edition, 1995, part V.5.9.1. pages 15–17. In this specific case an Andersen Cascade Impactor (ACI) was used. Results represented were obtained from ten cumulative actuations of a formulation. Deposition of the drug on each ACI plate was determined by high pressure liquid chromatography. The mass median aerodynamic diameter (MMAD) and geometric standard deviation (GSD) were calculated from plots of the cumulative percentage undersize of drug collected on each ACI plate (probit scale), against the upper cut off diameter for each respective ACI plate (log10 scale). The fine particle dose of each formulation was determined from the mass of drug collected on Stages 3 through to Filter (<4.7 $\mu$m) divided by the number of actuations per experiment.

Table 1 shows the MMAD characteristics of aerosol formulations containing beclomethasone dipropionate (BDP) (active material), glycerol as low volatility component and different mixtures of HFA 134a and HFA 227. As can be seen, the MMAD is substantially influenced by the ratio of the two fluorocarbons whereas FPD is substantially unaffected.

The presence of the low volatility component contributes to the modulation of the MMAD: its percent content (w/w) can be properly adapted to obtain the desired MMAD.

Table 2 shows the effects of valve chamber (also known as metering chamber) volumes at sump volume constant on the generation of aerosol clouds.

In particular, the data shown in Table 2 show that FPD increases with decreasing valve chamber volume and that FPD can be increased by more that 40% by reducing the volume of a valve metering chamber. MMAD or GSD are not conversely affected by changing the volume of the valve-metering chamber.

Therefore, the compositions of the invention consisting of aerosol drug solution in a mixture of 134a and 227 HFA propellants, a cosolvent and optionally a low volatility component, added into an aerosol inhaler having a chamber volume ranging from 25 to 50 µl, constitute a delivery system which allow improvement of the delivery characteristics of drugs to the lung by modulating the aerodynamic particle size and size distribution so that the pattern of deposition gives the desired clinical effect.

To obviate possible chemical stability problems of active ingredients in solution in HFA propellants metered-dose inhalers having part or all of their internal metallic surfaces consisting of stainless steel, anodized aluminium or lined with an inert organic coating can be employed.

TABLE 1

Effect of HFA 134a/HFA 227 mixtures upon the MMAD of pMDI solution formulation

BDP 250 µg/shot
Ethanol 15% (w/w)
Glycerol 1.3% (w/w)
HFA to 12 ml
Actuator = 0.30 mm

| HFA 227/ HFA 134a | MMAD (µm) | FPD (%) | $FPD_3 < 4.7 \mu m^*$ (µg) |
|---|---|---|---|
| 100:0 | 4.2, 3.9, 3.8 | 20, 20, 24 | 47, 45, 50 |
| 75:25 | 3.7, 3.7 | 25, 25 | 56, 57 |
| 50:50 | 3.4, 3.7 | 25, 25 | 56, 56 |
| 25:75 | 3.3, 3.2 | 27, 28 | 60, 62 |
| 0:100 | 2.8, 2.8 | 27, 27 | 58, 59 |

*Results normalized for 250 nominal dose.

TABLE 2

Effect of Valve Chamber Volume upon the FPD of pMDIs containing HFA 134a and HFA 227 Solutions Formulations BDP 50 µg/shot
Ethanol 13% (w/w)
Glycerol 1.3% (w/w)
HFA to 12 ml

| Chamber Volume (µl) | Propellant | FPD < 4.7 µm (µg) | MMAD (µm) | GSD | Metered Dose (µg) |
|---|---|---|---|---|---|
| actuator orifice 0.30 mm | | | | | |
| 25 | HFA 134a | 19.2 | 2.6 | 2.0 | 57 |
| 50 | | 13.9 | 2.8 | 2.1 | 49 |
| 100 | | 11.7 | 2.7 | 2.2 | 51 |
| 25 | HFA 227 | 16.4 | 3.6 | 2.1 | 58 |
| 50 | | 13.1 | 3.5 | 2.2 | 51 |
| 100 | | 12.6 | 3.5 | 2.2 | 49 |
| actuator orifice 0.25 mm | | | | | |
| 25 | HFA 134a | 26.0 | 2.8 | 1.9 | 55 |

What is claimed is:

1. A composition in the form of a solution comprising:
   a solubilized active material,
   a propellant comprising HFA 227 and HFA 134a, and
   optionally, a low volatility component, or a cosolvent, or both,
   wherein the ratio of HFA 227: HFA 134a ranges from 10:90 to 90:10 and
   the active material is an anticholinergic drug, a corticosteroid, or a β2 agonist.

2. The composition according to claim 1, wherein the low volatility component has a vapour pressure at 25° C. lower than 0.1 kPa.

3. The composition according to claim 1, wherein the low volatility component has a vapour pressure at 25° C. lower than 0.05 kPa.

4. The composition according to claim 1, wherein the cosolvent has a vapour pressure at 25° C. lower than 3 kPa.

5. The composition according to claim 1, wherein the cosolvent has a vapour pressure at 25° C. lower than 5 kPa.

6. The composition according to claim 1, wherein the cosolvent is an alcohol.

7. The composition according to claim 1, wherein the low volatility component includes a glycol, oleic acid or isopropyl myristate.

8. The composition according to claim 1, wherein the composition comprises not more than 20% by weight of the low volatility component.

9. The composition according to claim 1 comprising at least 0.2% by weight of the low volatility component.

10. An aerosol inhaler comprising a composition in the form of a solution wherein said solution comprises an active material, a propellant containing one or more hydrofluoroalkane(s), a cosolvent and optionally a low volatility component,
   wherein the particle MMAD produced by said aerosol inhaler is greater than 2 µm and the fine particle dose (<4.7 µm) is >30%,
   with the proviso that the active material is not Cyclosporin A.

11. An aerosol inhaler according to claim 10 that produces a particle MMAD greater than 2 µm and a fine particle dose (<4.7 µm) of >40%.

12. An aerosol inhaler according to claim 10 that produces a particle MMAD greater than 2 µm and a fine particle dose (<4.7 µm) of >50%.

13. The aerosol inhaler according to claim 10 having a chamber volume ranging from 25 to 40 µl yielding an increase of FPD compared to inhalers having chamber volumes larger than 50 µl.

14. The aerosol inhaler according to claim 10, wherein part or all of the internal surface(s) comprise stainless steel, anodized aluminium or an inert organic coating.

15. A delivery system for the administration of one or more drugs to the lung consisting of aerosol drug solution in a mixture of 134a and 227 HFA propellants, a cosolvent and optionally a low volatility component, in an aerosol inhaler having a chamber volume ranging from 25 to 40 μm, wherein the MMAD of the aerosol particles on actuation of the inhaler is not less than 2 μm and the fine particle dose (<4.7 μm) is at least 30%.

16. A delivery system comprising the composition of claim 1.

17. The delivery system of claim 16 that produces an aerosol comprising particles having a mass median aerodynamic diameter (MMAD) not less than 2 μm.

18. An aerosol inhaler comprising the composition of claim 1.

19. The aerosol inhaler of claim 18 that is a metered dose inhaler.

20. The aerosol inhaler of claim 18 that produces an aerosol comprising particles having a mass median aerodynamic diameter (MMAD) not less than 2 μm.

21. The composition of claim 1, wherein the active material comprises a β2 agonist.

22. The composition of claim 1, wherein the active material comprises a corticosteroid.

23. The composition of claim 1, wherein the active material comprises an anti-cholinergic drug.

24. The composition of claim 1 in the form of an aerosol.

25. An aerosol produced from the composition of claim 1 by a delivery system.

26. The aerosol of claim 25 that comprises particles having a mass median aerodynamic diameter (MMAD) not less than 2 μm.

27. The composition of claim 24, wherein the active material comprises an anticholinergic drug.

28. The composition of claim 24, wherein the active material comprises a β2 agonist.

29. The composition of claim 24, wherein the active material comprises a corticosteroid.

* * * * *